United States Patent [19]
Kishimoto et al.

[11] 3,980,437
[45] Sept. 14, 1976

[54] TEST STRIPS AND METHODS AND APPARATUS FOR USING THE SAME

[75] Inventors: Shinichi Kishimoto, Uji; Hiroshi Yamamoto, Kyoto, both of Japan

[73] Assignee: Kabushiki Kaisha Kyoto Daiichi Kagaku, Japan

[22] Filed: Dec. 18, 1975

[21] Appl. No.: 641,829

[30] Foreign Application Priority Data
Dec. 21, 1974 Japan.......................... 49-155888[U]
Jan. 17, 1975 Japan................................ 50-7005

[52] U.S. Cl........................... 23/253 TP; 356/199; 356/209
[51] Int. Cl.²................. G01N 21/30; G01N 21/48; G01N 31/22; G01N 33/16
[58] Field of Search................. 23/253 TP; 356/199, 356/209

[56] References Cited
UNITED STATES PATENTS
| | | | |
|---|---|---|---|
| 3,827,808 | 8/1974 | Cho | 356/199 |
| 3,907,503 | 9/1975 | Betts et al. | 23/253 TP |

*Primary Examiner*—Robert M. Reese
*Attorney, Agent, or Firm*—Steinberg and Blake

[57] ABSTRACT

A test strip of the type which is dipped into a liquid such as urine for indicating by color information with respect to the liquid. The test strip has a transparent backing on one side of which is located a color-reaction paper with a fastening layer situated between the paper and the backing for fastening the paper to the backing. The fastening layer is opaque and non-reflecting with respect to light, so that while light can pass freely through the backing it will reflected by the color-reaction paper without passing through the backing. The test strip is moved perpendicularly across an optical axis along which light is directed with the light traveling first through the transparent backing and then being reflected by the color-reaction paper. Signals are generated from the light passing through the backing and the light reflected by the color-reaction paper, with the timing of the signal from the reflected light being controlled by the signal from the light which has passed through the transparent backing. The signal from the light which has traveled through the backing is utilized to initiate a time interval after which the signal from the reflected light is generated so as to assure that the operation of the structure providing the signal from the reflected light takes place when the color-reaction paper intersects the optical axis.

18 Claims, 21 Drawing Figures

TEST STRIPS AND METHODS AND APPARATUS FOR USING THE SAME

BACKGROUND OF THE INVENTION

The present invention relates to test strips of th type used to indicate by color properties with respect to a liquid such as urine in which the test strip is dipped. Also, the present invention relates to methods and apparatus for utilizing such test strips.

Thus, the present invention relates to a method and apparatus for measuring light-reflectivity of colorreaction reaction test paper utilized for various purposes such as testing of liquid samples such as urine, and the invention also relates to the construction of the test strip itself.

Color-reaction test papers are widely used as a simple means for analyzing liquids. For example in many hospitals and clinics it is conventional to utilize test papers for measuring, as a part of a clinical examination, concentrations of glucose, protein, pH, bilirubin, etc. in urine.

Thus, when such a test paper is dipped into a liquid such as urine, the test paper will have a color-reaction to an extent which will be indicative of the concentration of the particular liquid component which is to be measured. Judgment of the degree of color-reaction of the test paper is generally carried out by comparison with a color-reaction sample at a standard concentration of the liquid component which is to be measured. This comparison of tone utilizes only the naked-eye observation of skilled technicians. In many cases, particularly with complex test paper, it is necessary to carry out accurate comparison with corresponding color-reaction samples for each item. These operations are extremely troublesome because the tone of the color-reaction test paper piece often will change with the passage of time. Conventionally, the skilled technician will make a judgement in a relatively short time and will utilize his memory of the color-reaction tone as obtained through experience. However, such results are defective and highly inaccurate inasmuch as the judgment is influenced in a highly subjective manner according to the individual differences of the technicians who make the judgment. Thus it is impossible to achieve the desired degree of objectivity with such conventional procedures.

Moreover, due to the great increase in clinical examinations in recent years, there has been a large increase in the number of items and samples which must be measured, and thus the number of technicians available for carrying out these operations is far too small to meet the required demand. For such reasons it has become necessary to prove the efficiency with which the examination procedures are carried out as well as to save personnel.

SUMMARY OF THE INVENTION

It is accordingly a primary object of the present invention to provide a test strip as well as a method and apparatus for using the same, all of which are capable of avoiding the above drawbacks encountered with conventional procedures and structures.

Thus, it is a primary object of the present invention to provide not only a test strip but also a method and apparatus all of which make it possible to carry out highly accurate measurements by mechanizing the color-reaction judgment operations.

Also it is an object of the present invention to be able very efficiently to carry out a large number of different types of measurement operations.

In addition it is an object of the present invention to provide a test strip according to which the color-reaction paper will cooperate with light impinging thereon in such a way that substantially all of the light is reflected and none is transmitted through the color-reaction paper, in order to greatly improve the accuracy of the measurement.

Furthermore, it is an object of the present invention to provide a test strip and method and apparatus for using the same according to which the results will not be undesirably effected even if several color-reaction papers on a common backing are not precisely situated at given distances one from the next along the backing and even if the transportation of the test strip with respect to light impinging thereon is not carried out at a precise constant speed.

According to the invention the test strip includes a transparent backing on one side of which is located one or more color-reaction papers with a fastening means being situated between each color-reaction paper and the backing g for fastening the color-reaction paper thereto. The fastening means is substantially opaque and non-reflecting with respect to light, so that while light can pass freely through the transparent backing, when the light encounters the color-reaction paper, the fastening means prevents the light from traveling beyond the color-reaction paper so that substantially all of the light is reflected from the color-reaction paper. According to the method and apparatus of the invention, the light passing through the transparent backing and the light reflected from the color-reaction paper is utilized for generating a pair of signals by way of one detecting means situated behind the strip on the side thereof opposite from the light source to receive light which passes through the backing and another detecting means which is situated on the same side of the strip as the light source to receive light reflected from the color-reaction paper. Because of the presence of the opaque fastening means between the color-reaction paper and the transparent backing, the light received by this pair of detecting means will differ sharply to provide a very strong differentiation in the signals which can be utilized for accurately judging when the signal of the light reflected by the color-reaction paper is to be detected. Suitable electronic circuitry is provided for giving in an automatic manner an indication of the concentration of the liquid component which has been tested. Furthermore, apparatus is provided according to the invention for substantially completely mechanizing the entire operation.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
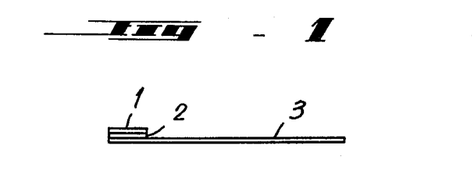
FIGS. 1–3 are schematic side views of different embodiments of test strips.

Referring to FIG. 1, the test strip illustrated therein includes a backing 3 which acts as a supporting structure for carrying the color-reaction test paper piece 1, fastened to the backing 3 by way of a fastening means in the form of a bonding layer 2. Thus, through the bonding layer 2 the support structure 3 supports the test paper piece 1.

Figure 2:
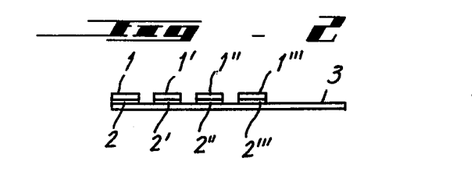

It is also possible to utilize a complex test paper, as illustrated in FIG. 2, according to which the backing 3, which is of an elongated configuration, carries a plurality of color-reaction test paper pieces 1, 1', 1'', etc. All of these color-reaction papers are fastened to the backing 3 by way of the corresponding bonding layers 2, 2', 2'', etc., which form the fastening means for the several color-reaction papers. Such a complex test paper may be utilized for measuring a number of different items such as, for example, glucose, protein, etc., simultaneously with respect to a single sample.

The color-reaction paper reacts with the component which is to be measured and produces a color-reaction effect the degree of which corresponds to the concentration of the liquid component which is to be measured. Judgment of the degree of color-reaction of the test paper piece 1 is generally carried out by comparison with a color-reaction sample of a standard concentration of the liquid component to be measured, and when this comparison is made by technicians the abovementioned drawbacks with respect to subjectivity of the results will obtain.

In order to mechanize the determination of the degree of color-reaction of the color-reaction test paper, the reflectivity of the color-reaction paper will generally be measured. For this purpose the wavelenngth of light is selected to have such a value that the characteristic of the spectral reflectivity of the color-reaction paper will vary greatly with respect to the concentration of the particular liquid component which is to be measured.

Figure 5:
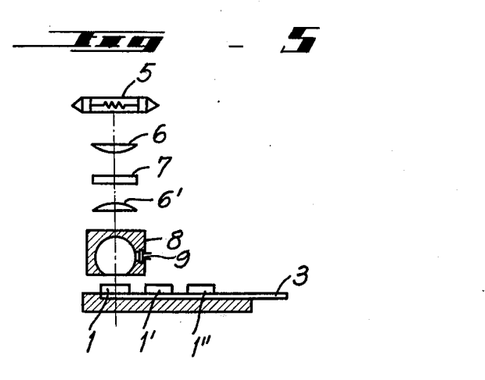
FIG. 5 is a partly sectional schematic elevation of an apparatus for use with a test strip.

Various types of measurement of reflectivity can be considered, such as, for example, a type of measurement according to which the angle of incidence and the angle of reflection of the light are both 45°. In order to avoid an undesirable influence from lack of evenness of the surface of the color-reaction paper and lack of uniformity of the color-reaction, it is desirable to collect light from the largest possible area of the surface of the color-reaction paper, with the widest possible angle, and then to measure the mean value. For such a purpose it is desirable that the diameter of the bundle of light rays impinging on the test paper be relatively large. A conventional technique for such stabilized measurement of reflectivity is to utilize an integration sphere type of reflectivity unit 8, as shown schematically in FIG. 5.

However, while it is desirable to have the largest possible area of the color-reaction paper for the reasons set forth above, it is on the other hand also desirable that the size of the color-reaction paper be small for advantages to be achieved in connection with production and use of the test strip structure. In order to measure reflectivity of the color-reaction paper 1 with the integration sphere 8, the accuracy of the position of the test paper 1 with respect to the integration sphere 8 is important.

Figure 4A:
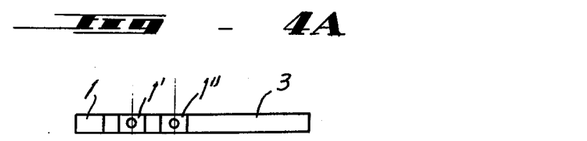
FIGS. 4A and 4B are respectively plan and side views illustrating the arrangement of color-reaction papers along a backing.
Figure 4B:
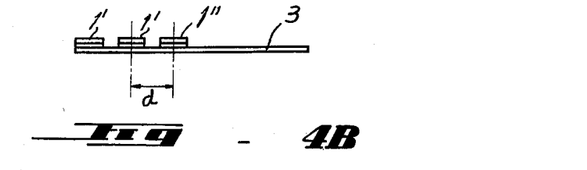

For the purpose of automatically measuring the degree of color-reaction of a test paper such as pieces 1 and 1' in succession by way of mechanization of the measurement of a complex test strip having thereon a plurality of color-reaction papers 1 and 1', two different procedures may be considered as follows:

(A) The interval or space between a pair of neighboring color-reaction papers 1 carried by the backing 3, as illustrated by the distance $a$ in FIG. 4B, is maintained constant. Thus, as is apparent from FIGS. 4A and 4B, the distance from the center of one color-reaction paper to the center of the next color-reaction paper is maintained constant along the test strip. Thus, the distance from the center of the part of one test paper piece on which the bundle of light rays from the light source falls during the measurement time to the center of the next test piece which will subsequently receive the light is constant. The test strip is moved at a constant speed and measurements are carried out in succession at a constant time interval with such a procedure. The test strip may be continuously moved or the alternative may be stopped for a given interval during the time when a measurement operation is going forward in a manner illustrated in FIG. 5. Thus in FIG. 5 there is an optical means for directing light along an optical axis shown with the dot-dash line in FIG. 5, this optical means including the light source formed by the lamp 5, a lens 6 for making parallel the bundle of light rays from the light source lamp 5, a filter 7 which will provide light with a desirable wavelength, a lens 6' for condensing the light rays which have passed through the filter 7, and an integration sphere 8 which carries a detecting means 9 which serves to receive light reflected from the color-reaction papers 1, 1', etc., the test strip in FIG. 5 being mounted on a conventional support which can be moved with respect to the optical means, or if desired the optical means can be moved with respect to the test strip in such a way that at given time intervals the light will impinge on the test paper to be reflected and received by the detecting means 9. Thus, the carriage which carries the test strip in FIG. 5 may be moved continuously across the optical axis of the optical means or it may be stopped in its movement during the intervals when measurement of reflected light is carried out.

Figure 6A:
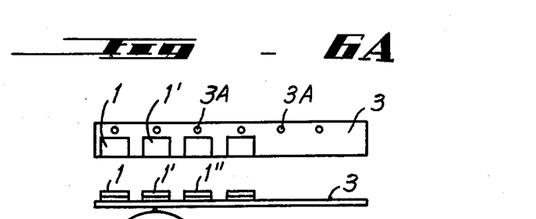
FIGS. 6A and 6B are respectively schematic top plan and side views of a further embodiment of a test strip structure and mechanical structure for utilizing the same.
Figure 6B:
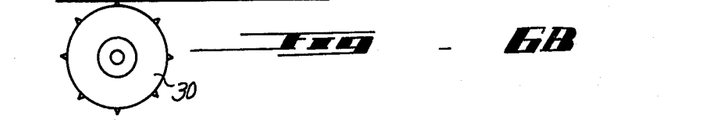

(B) It is also possible to provide an arrangement according to which the backing 3 of the test strip has openings or holes 3A situated at constant intervals one from the next, as illustrated in FIG. 6A. In this case the several color-reaction test papers 1, 1', etc. are fastened to the test strip backing 3 by way of suitable bonding layers precisely at positions corresponding to the positions of the row of holes 3A. As is indicated in FIG. 6B, with such an arrangement it is possible to provide a sprocket 30 having teeth which will successively engage the successive holes 3A during roatry movement of the sprocket 30, so that in this way the test strip will be caused to move longitudinally enabling measurement to be made in succession of the several test papers in synchronism with the angular movement of the sprocket 30. In this case also the test paper may be continuously moved or in the alternative it may be stopped during the intervals when measurement of reflected light is carried out.

In the case of procedure A (referred to above) it is essential that the intervals or distances between the several color-reaction papers be maintained constant while if measurement is to be carried out with continuous movement of the test paper it is also essential that the speed of movement of the test paper be maintained constant.

In the case of procedure (B), it is essential to attach the several color-reaction papers at positions corresponding to those of the holes which are situated at constant intervals one to the next.

Thus, in the case of both of the above procedures (A) and (B), the test paper pieces must be mounted on the backing at constant distances one from the next. In order to achieve effective reflectivity measurements over a large area of the pieces of test paper, highly accurate positions of the attachment of the test paper to the backing are essential.

As will be apparent from the description below, according to the present invnention it is not essential to attach the several color-reaction papers to the backing at precisely constant intervals one from the next. Moreover it is possible to make accurate reflectivity measurements even if the speed of movement of the test paper is unstable or not constant to a given extent.

A specific example of a complex test strip according to the invention has been produced in connection with automatic urine analyzing procedures. The complex test paper of the invention will have an elongated ribbon-shaped backing 3 which is transparent and made of a suitable resin or the like. This backing 3 carries by way of the fastening means 2, 2', etc., a series of color-reaction papers 1, 1', etc. which are utilized to detect different constituents, respectively, such as urine sugar, urine protein, pH, urine ketones, urine bilirubin, occult blood, etc.

Figure 14:
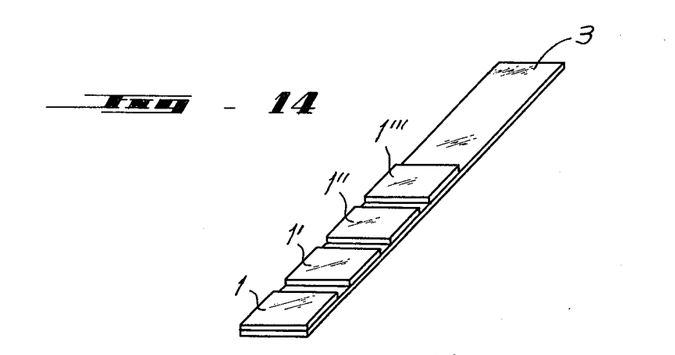
FIG. 14 is a perspective illustration of a conventional test strip.

While the complex test strip of the invention will in general have a configuration as illustrated in FIG. 14, the several color-reaction papers 1, 1', etc., are fastened to the transparent backing 3 by way of a plurality of fastening means 2, 2', etc., which are in the form of layers of adhesive tape or the like which have the property of being substantially opaque and non-reflecting with respect to light. Thus, light received by the backing 3 at intervals between the color-reaction papers will pass freely through the backing 3. The several color-reaction papers 1, 1', etc., are fastened in the above manner to the backing 3 for the purpose of making successive measurements of, for example, pH, urine sugar, urine protein, etc. Alternatively, the complex test paper may carry a standard reflection color-reaction paper 4 shown in FIG. 3, in addition to the color-reaction papers 1, 1', etc., so that from the standard color-reaction paper 4 it is possible to obtain a standard against which the reflectivity of the other color-reaction papers can be measured. In this way it is possible, as will be set forth in greater detail below, to achieve an automatic urine analysis.

Figure 15:
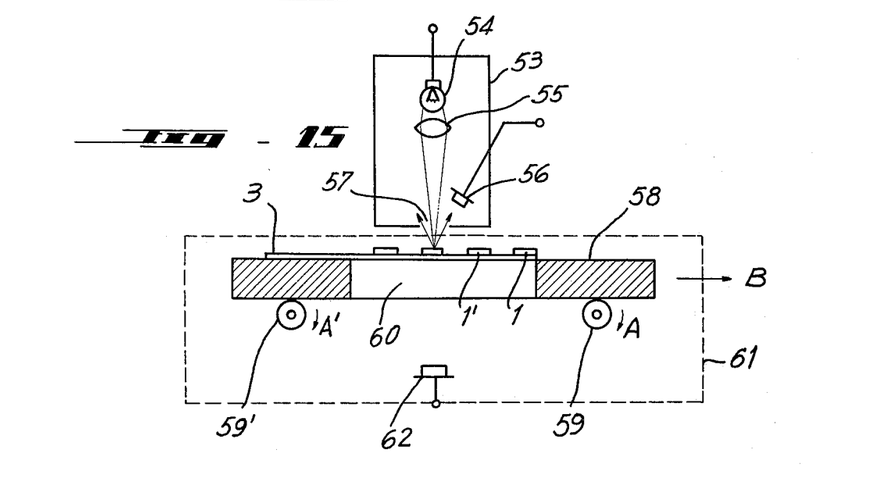
FIG. 15 illustrates a method and apparatus of the invention utilized with a conventional test strip of the type shown in FIG. 14.

FIG. 15 schematically shows an automatic urine analysis and method which can be utilized by the invention, although FIG. 15 shows the method and apparatus of the invention used with the conventional test strip, so as to indicate the advantages achieved by way of the present invention. Thus, referring to FIG. 15, an optical means 53 is provided in the form of a reflective photometer, and in cooperation therewith there is schematically illustrated a transporting means 61 for transporting the test strip. The reflective photometer 53 has the light source lamp 54, a condenser lens 55 and a light-detecting means 56. These units are optically isolated from the exterior by way of outer housing of the unit 53, this isolation from the outside light being complete except for the measuring window 57.

The transporting means 61 takes the form of a carriage 58 capable of moving horizontally and carrying the complex test paper at a predetermined position. Rotary drive shafts or rollers 59 and 59' cooperate with the carriage 58 to move the latter back and forth to the right and left, as illlustrated in FIG. 15. Thus, in this way the carriage 58 will carry out a reciprocating movement so that the test strip on the carriage 58 will also make the same reciprocating movement. In this way the color-reaction papers 1, 1', on the backing 3 will successively be displaced horizontally immediately below the measuring window 57 of the reflective photometer 53. As a result, each of the color-reaction 1, 1' will reflect a certain amount of the light from the light source 54 in succession to the light-detecting means 56 which detects the light transmits the detected light in the form of a corresponding electrical signal.

Figure 16:
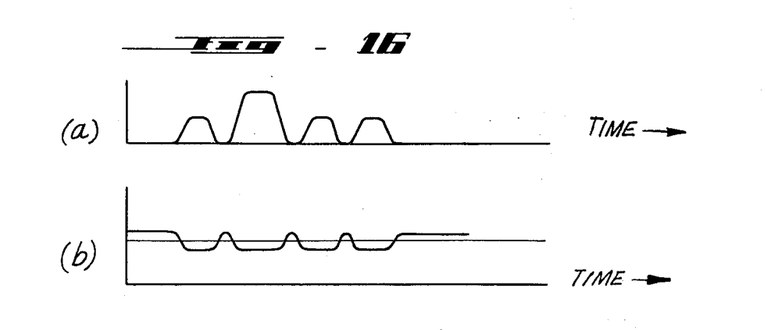
FIG. 16 has graphs showing results achieved with the method and apparatus of the invention illustrated in FIG. 15 but with a conventional test strip structure.

The graph (a) of FIG. 16 shows a series of light signals derived from the detecting means 56. In the graph (a) time is prodded along the abscissa, while intensity of light reflection is prodded along the ordinate. The wave portions of the curve of graph (a) extending upwardly from the abscissa correspond to the signals derived from the successive color-reaction papers 1, 1', etc., respectively, while the lowermost portions of the curve situated directly at the abscissa correspond to the backing 3. Thus, this curve indicates that there is no reflected light from the backing which is transparent and has a high degree of light transmissivity, while the reflected light corresponds to the degree of color reaction obtained from the color-reaction papers 1, 1', etc., respectively.

The carriage or manipulator 58 is provided at a position corresponding to that of the test strip with an opening 60 which passes completely through the carriage 58 along at least that part of the length of the backing 3 where the several color-reaction papers are located. At the side of the backing 3 opposite from the optical means 53 there is a detecting means 62 so that the light which passes through the test strip will be received by the detecting means 62. As a result of the horizontal movement of the color-reaction papers, the light-detecting means 62 will provide signals as illustrated by the graph (b) of FIG. 16, this graph having the same graduations along the abscissa and ordinate as the upper graph of FIG. 16. Thus, the lower curve of FIG. 16 indicate that the intensity of transmitted light is great at those intervals when the backing 3 which is transparent moves across the measuring window 57, while the transmitted light intensity is relatively small at the intervals when the color-reaction papers 1, 1', etc., move across the measuring window 57. Thus it will be seen that the peaks of the curve of graph (b) of FIG. 16 are in alignment with the lowest parts of the curve of graph (a) of FIG. 16.

Thus, the signals achieved from the detecting means 56 will contain information with respect to the degree of color-reaction of the color-reaction papers 1, 1', etc. In processing these signals it is important accurately to carry out the digitalization at precisely determined intervals. For this purpose it is possible and desirable to utilize the signals derived from the light detector 62 as synchronization signals determining the timing of the operation of the detecting means 56.

When making use of the above automatic measurement method and apparatus of the invention, if conventional complex paper as shown in FIGS. 14 and 15 is utilized, serious drawbacks are encountered in that the light-transmissivity of the color-reaction papers 1, 1', etc., is not sufficiently small, or in other words these color-reaction papers have a property of transmitting too much light therethrough. Particularly when the color-reaction papers are dipped in a urine sample and are made uniformly wet over a large area, they have a great degree of light transmission, although the degree of light transmission may vary with the degree of color-reaction. In addition, the interval from one color-reaction paper to the next along the backing 3 is not always constant and may have randomly scattered values. As a result, the areas of the portions of the backing 3 between successive color-reaction papers are not constant and uniform, and in addition the actual amount of light passing through the test strip varies so that the output signal from the detecting means 62 cannot be utilized for the purpose of achieving accurate synchronization signals.

As will be apparent from the description below, if a test strip according to the present invention is utilized with a method and apparatus as shown in FIG. 15, it is possible to eliminate the disadvantages set forth above. Thus, the complex test strips of the invention have color-reaction papers 1, 1', etc., thereon which do not transmit light when they are wet with a urine sample and are capable of providing accurate synchronization signals.

Figure 7:
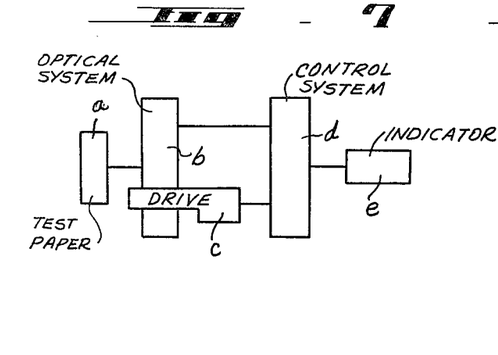
FIG. 7 is a schematic block diagram illustrating the method and apparatus of the invention.
Figure 11:
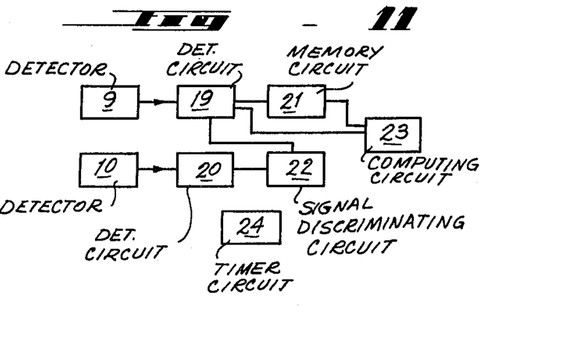
FIG. 11 is a block diagram illustrating the electronic circuitry of the invention.

Referring now to FIG. 7, there is schematically illustrated therein various units of the invention for carrying out the method of the invention. Thus, the block a in FIG. 7 indicates a test strip of the invention as illustrated, for example, in FIG. 17. The block b illustrates the optical system which may have the structure shown in FIG. 8, for example, while the block c indicates the transporting means as shown in FIG. 9, for example. The block d represents an electrical means in the form of a control system as illustrated in FIG. 11, while the block e is an indicating system for indicating the desired information.

Figure 3:
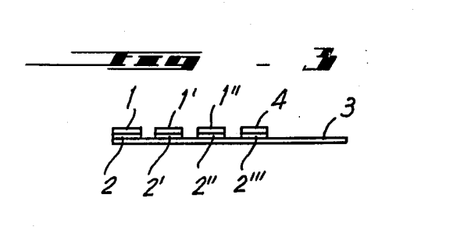
Figure 17:
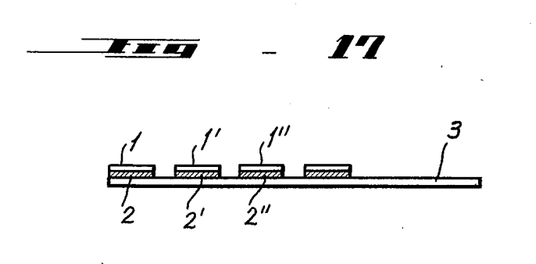
FIG. 17, is a schematic side elevation of a test strip having the structure of the present invention.

With respect to a of FIG. 7, the test strip may have a structure as shown in FIGS. 3 or 17 according to which the transparent backing 3 has the several color-reaction papers on one side thereof with the plurality of fastening means 2, 2', etc. situated between and fastening the color-reaction papers to the backing, the fastening means being opaque and substantially non-reflective with respect to light, as pointed out above.

Figure 8:
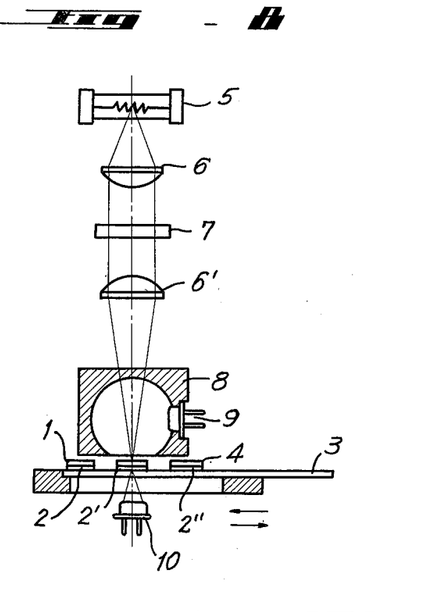
FIG. 8 is a partly sectional schematic illustration of a method and apparatus of the invention utilizing a test strip of the invention.
Figure 9:
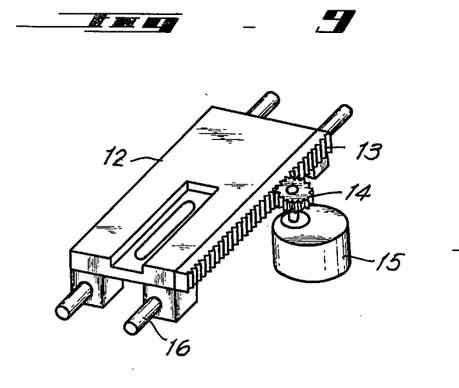
FIG. 9 is a partly schematic perspective view showing details of the structure of FIG. 8.

Referring now to FIG. 8, which illustrates the optical means b of FIG. 7, it will be seen that this structure corresponds to that described above in connection with FIG. 5, except that in this case the carriage which carries the test strip 3, provided with a standard color-reaction paper 4 as shown in FIG. 3, is formed with an opening through which the light can pass to the detecting means 10 of FIG. 8 which corresponds to the detecting means 62 of FIG. 15. In FIG. 8, however, the optical means includes the integration sphere 8 rather than the photometer unit 53 of FIG. 15.

Figure 10:
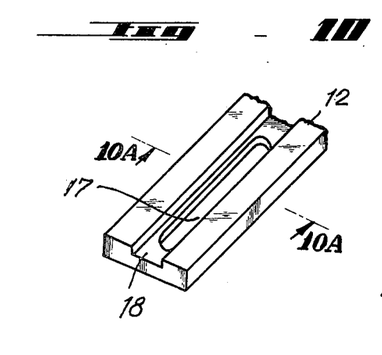
FIG. 10 is a fragmentary perspective view showing a carriage of FIGS. 8 and 9.
Figure 10A:
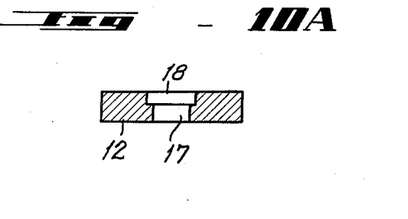
FIG. 10A is a transverse section of the structure of FIG. 10 taken along line 10A—10A of FIG. 10 in the direction of the arrows.

With respect to the filter 7, it is to be noted that the spectral wavelength of this filter is determined according to a value where the spectral reflectivity of the test paper will vary greatly in response to the concentration of the liquid component which is to be measured. Thus, with the structure of FIG. 8 the reflected light will be received by the detecting means 9 whereas the light which passes through the backing will be received by the detecting means 10. Referring to FIG. 9, which shows the transporting means c of FIG. 7, this transporting means includes a slide carriage 12 which carries the test strip and which is driven from a motor 15 through a rack 13 which is fixed to one side of the carriage 12 and which meshes with a pinion 14 which is rotated by the motor 15. This motor 15 is connected to the pinion 14 through a suitable transmission. As is shown most clearly in FIG. 10, as well as 10A, the carriage 12 is formed with an elongated slot 17 through which the light can freely pass while this slot 17 communicates with the lower portion of a groove 18 which receives the test strip for accurately positioning the latter on the carriage 12. The carriage 12 is guided for sliding movement by suitable guide structure 16 schematically illustrated in FIG. 9. This guide means 16 serves to provide for the carriage 12 a smooth movement and is arranged so that it is possible for the carriage 12 to carry out one reciprocating motion in response to a driving signal received from the control means of FIG. 11.

Referring now to FIG. 11, the control means includes a timing circuit means 24 as well as a pair of detector circuit means 19 and 20 respectively connected with the pair of detecting means 9 and 10 to respectively receive inputs therefrom. A discriminating circuit means 22 is connected between the detecting circuit means 20 and the detecting circuit means 19, while a memory circuit means 21 is connected between the detecting circuit means 19 and a computing circuit means 23. It will be noted that the detecting circuit means 19 also is connected directly to the computing circuit means 23.

The timing circuit means 24 is provided in order to ensure that there will be a sufficient reaction time for the color-reaction paper. When the operator starts the timing circuit means 24, the initiation of the operation of the motor 15 will be delayed by a certain time interval ensuring that the required color-reaction has had sufficient time to develop, so that in the event that the operator places the test strip on the carriage 12 immediately after dipping the test strip in urine, there will nevertheless be a sufficient time before the operations are carried out in order to assure that accurate results will be achieved.

The detecting circuit means 19 and 20 receive from the detecting means 9 and 10, respectively, inputs which are converted by the detecting circuits means 19 and 20 into voltages. In order words the current signals from the detectors 9 and 10 are transformed by the detecting circuits 19 and 20 into corresponding voltages, respectively. The signal discriminating circuit 22 is provided in order to confirm, from a signal received from the detecting means 10, that the color-reaction paper has occupied the position to be illuminated by the optical system. In other words, the discriminator circuit 22 responds to impingement of the light on the leading edge of the color-reaction paper, this response being brought about by the fact that the light transmitted through the transparent backing 3 suddenly terminates when the leading edge of the color-reaction paper reaches the light. Thus, as the leading edge of the color-reaction paper cuts into the light beam the amount of the light received by the detecting means 10 sharply diminishes and in this way it is possible to pick up a signal indicating that the color-reaction paper has approached a position where it is about to be properly situated for transmitting reflected light to the detecting means 9 in order to give a reading of the intensity of the color. The discriminating circuit 22 consists of a comparator circuit with a certain value and a delay circuit for issuing measuring instructions to the detecting circuit 19 at a time interval somewhat later than the timing of the position-detecting operation.

The memory circuit 21 memorizes the signal which serves as a standard for reflectivity of the time computing of the reflectivity is carried out. The light reflected from the standard color-reaction paper 4 on the backing 3 serves as the standard. The computing circuit 22 compares the reflected light signal of a particular color-reaction paper 1', 1'', etc. with the standard reflectivity signal memorized by the memory circuit 21, and on this basis the computing circuit means 23 computes the reflectivity of the particular color-reaction paper from which light is reflected to the detecting means 9.

The indicating system represented by the block e in FIG. 7 consists of a comparator circuit and indicating elements for indicating the degree of color-reaction of the color-reaction paper 1', 1'', etc. in ranks of several stages. This system determines the color-reaction rank of the signal indicating the reflectivity from the control system computing circuit 23, and a corresponding result is indicated. In other words, there are several successive stages or ranges of color and the indicating means indicates in which range the particular color falls of a particular color-reaction paper, so as to give an indication in this way of the concentration of the particular liquid component which is being tested.

The apparatus of the invention is operated, in accordance with the method of the invention, as follows:

First, the operator will dip the test strip into the liquid sample which is to be tested, and at the same time the timing circuit means 24 is set into operation. While this timing circuit means 24 operates, the operator will place the test strip, which has just previously been immersed in the sample on the slide carriage 12 in such a way that the standard reflection color-reaction paper 4 is positioned nearest to the operator. After a given reaction time has elapsed, the timing circuit 24 will send a signal to the motor 15 to initiate the operation thereof so that the slide carriage 12 with the test strip thereon will now start to move, and now the test paper will pass through the optical system. The arrangement is such that the slide carriage 12 will make one reciprocating motion in response to one driving signal from the timing circuit means 24, so that the test paper passes twice through the optical system. The drive is such that the entire strip is first moved completely through the optical system, and then upon the return movement the several readings are taken, so that in this way the first reading will be from the standard color-reaction paper 4, providing in this way the standard against which the remaining readings will be compared. Thus, during this return movement there will be at the detecting means 9 a signal as illustrated by graph (A) of FIG. 12, while at the detecting means 10 there will be a signal as indicated by the graph (B) of FIG. 12.

Figure 12:
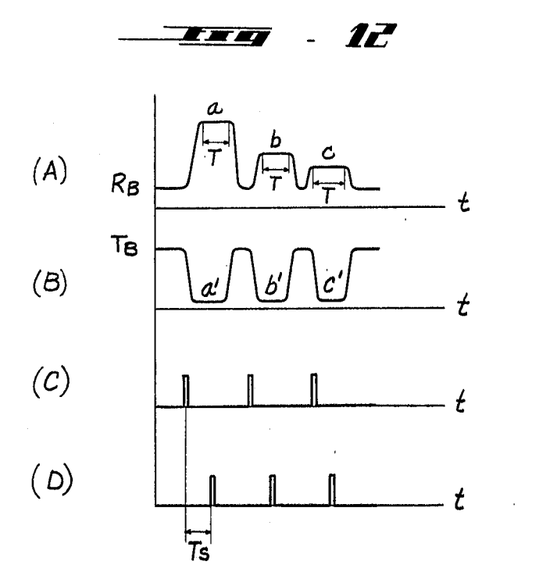
FIG. 12 is a graph having various curves indicative of the operation of the method and apparatus of the invention with the test strip of the invention.

The level $R_B$ of FIG. 12, at graph (A) indicates the reflected light signal level of the backing 3, while the level $T_B$ of graph (B) of FIG. 12 indicates the signal level of the light which has passed through the transparent backing 3. The portion $a$ of graph (A) indicates the state when the light impinges on the standard reflection reaction paper 4, while the succeeding portion $b$, $c$, indicate the signals when light impinges on the corresponding successive color-reaction papers, respectively. The reflectivities of the corresponding color-reaction papers will be known by comparing the signal levels $b$, $c$, with the signal levels $a$, respectively.

On the other hand, the parts $a'$, $b''$, $c'$, etc. of graph (B) of FIG. 12 indicate the signal resulting from transmission of light through the standard reflection color-reaction paper 4, and the successive color-reaction papers, with of course this light-transmission being further influenced by the bonding layer or fastening means between the color-reaction papers and the backing. Thus it will be seen that the transmissivity of the standard reflection paper 4 and the successive color-reaction papers is exceedingly small as compared with the light-transmissivity of the backing which is transparent, and while the signal of the light passing through at the levels of the portions $b'$, $c'$, etc. of graph (B) may vary with the degree of color-reaction, it is possible to regard these portions $a'$, $b'$, $c'$, etc., as being of approximately equal level.

Thus, it is possible to know whether or not a color-reaction paper is present at the optical means to reflect light, by transmitting the light-transmission signal of the detecting means 10 to the discriminating circuit means 22.

The graph (C) of FIG. 12 illustrates the signals indicating the position of the color-reaction paper, as discriminated by the light passing through the transparent backing. The graph (D) of FIG. 12 is a graph of signals which are transmitted to the light-detecting means 9 in order to start the operation thereof so that the reflected light will be measured and then compared by the computing circuit means as set forth above. It will be noted that the discriminating circuit means 22 provides through the signals of graph (B) an initiation of the operation of the detecting circuit means 19 only after a certain time interval $T_S$ as is apparent from a comparison of the graphs (C) and (D). Thus, when the transmitted light falls off sharply as indicated by the portion $a'$ of graph (B), the discriminating circuit means will with a certain time delay $T_S$ initiate the operation of the measurement of the reflected light which in this case will of course be reflected from the standard color-reaction paper 4, and in the same way the succeeding measurements are made with the same delay after it is detected that the transmitted light has sharply fallen off. Of course this first reading from the standard color-reaction paper is memorized by the memory circuit 21. Then when the first color-reaction on test paper 1' is detected, the reflected light is detected with the above time delay $T_S$. The reflected light signal b of the detected color-reaction paper 1' assuming that the latter is the one immediately following the standard paper 4, is transmitted to the computing circuit 23 and is compared with the standard reflected light signal $a$, so as to obtain the reflectivity. With respect to the signal indicating the resulting reflectivity, the corresponding color-reaction rank is determined by the indicating circuit e shown in FIG. 7, and this is indicated as a rank or stage of color reaction of the corresponding color-reaction paper.

In the same manner the several color-reaction degrees of each of the color-reaction papers on the backing 3 is indicated, and the slide carriage of course returns to its original position in order to complete one measuring operation.

It is to be noted that in the above measuring operations, the flat portions of the reflected light signals a, b, c, etc. of graph (A) of FIG. 12 has a certain width T, so that insofar as the timing of the measurement instruction signal shown in graph (D) is concerned, it is not critical if this signal is not precisely at a certain point, so long as it occurs during the flat portion of the signal shown in graph (A). Thus a certain tolerance may be provided with respect to the speed of movement of the test strip. This can be achieved because the time delay $T_S$ is determined in such a way that when the color-reaction paper is moved with a certain constant speed the measurement is made approximately at the middle of the flat portion of each signal.

As has been indicated above the present invention provides a number of advantages. Thus, even if the color-reaction papers are not uniformly distributed along the backing and even if the speed of movement of the strip is not precisely uniform, it is possible to make accurate measurement of the reflectivities of the color-reaction papers. Due to the mechanization of the measurement, a great number of objective measurements can be carried in a relatively short time.

The complex test strip of the invention has a number of features. Thus, referring to FIG. 17, the color-reaction papers 1, 1',1'', etc. are attached to the backing 3 which is made of a transparent material by way of the bonding layers 2, 2',2'', etc., which take the form of adhesive tape which is adhesive at both of its faces and which in addition is black so as to serve not only as a fastening means but also as a light shield. The conventional transparent or colorless adhesive tape will permit light to pass through so that if such adhesive layers are used there will be a lack of precision and a considerable uncertainty in the generation of the synchronizing signal. With the complex test strip according to the invention, however, the light is sufficiently intercepted by the opaque fastening means so that a highly reliable precise generation of the synchronizing signal can be achieved.

Figure 18:
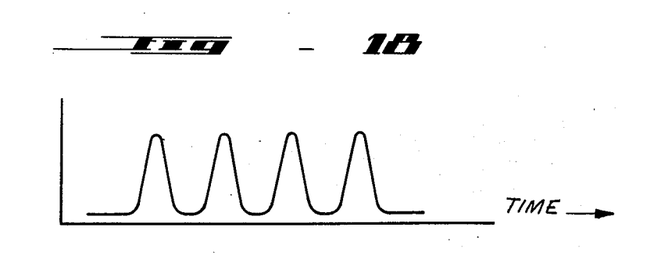
FIG. 18 is a graph illustrative of the difference which is achieved when utilizing the test strip of the invention with the method and apparatus of FIG. 15.

FIG. 18 shows in graph form the results achieved when using a strip of the invention as illustrated in FIG. 17, for example, or as illustrated in FIG. 3, for example, in the apparatus of FIG. 15. Thus, the curve of FIG. 18 represents the signal derived from the detecting means 62 with the test strip of the invention utilized in the structure of FIG. 15. A comparison between the graph (b) of FIG. 16 and the graph of FIG. 18 clearly demonstrates the advantages achieved by way of the test strip of the present invention.

The bonding layer which serves as a light shield need not necessarily be in the form of black adhesive tape. It can, for example, have other colors such as blue, red, brown, etc. The only essential point is that the amount of light passing through be diminished as much as possible so as to obtain a highly reliable generation of the synchronizing signal. On the other hand, if the light reflected by the light shield 2 passes through the color-reaction surface and is received by a detector such as the detector 56 or the detector 9, then of course a certain error will be contained in the measurement signal. Therefore, in the case of colors such as blue, red or brown, for the adhesive tape, it is important to use with the test strip of the invention not one of these colors which has the least possible surface reflection. Of course black adhesive tape will have very little if any reflection.

Thus, the complex test strip according to the invention improves the measurement accuracy in examination of liquids such as urine. Inasmuch as the light shields 2, 2',2'' which also serve as bonding layers do not let light be either reflected or transmitted, there are only exceedingly small measurement errors due to the scattered values of the thicknesses of the color-reaction test papers 1, 1',1'',etc., and a highly reliable generation of the synchronizing signal is assured.

Figure 13:
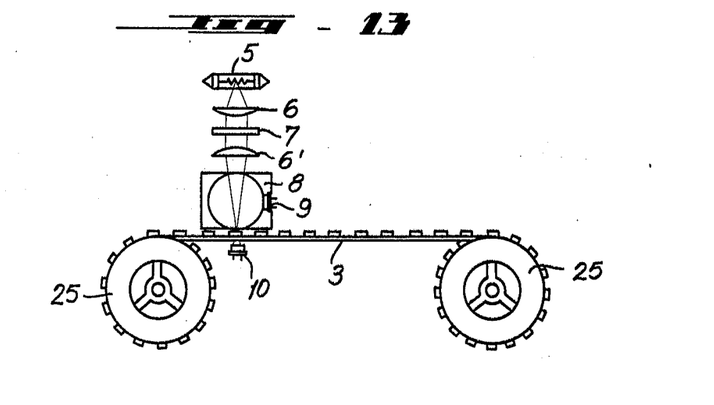
FIG. 13 is a schematic elevation of a further embodiment of a method and apparatus according to the invention utilizing a test strip structure of the invention.

It is to be noted that the use of a reciprocating carriage for the transporting means is not essential. Thus, referring to FIG. 13, it will be seen that it is possible to attach a series of test strips one to the next in end-to-end relation. This attached series of test strips will thus form a long tape which is flexible and which may be wound on a rotary support such as the left support 25 shown in FIG. 13. The right rotary support 25 is the equivalent of a take-up spool while the left rotary support 25 is the equivalent of a supply spool. These spools are turned in a clockwise direction, as viewed in FIG. 13, so that the continuous test strip 3 moves from the left toward the right, as viewed in FIG. 13, thus providing in this way a series of readings for an extremely large number of color-reaction papers in an extremely rapid manner. Of course the optical means of FIG. 13 is identical with that of FIGS. 5 and 8, for example and will achieve all of the results of the invention in connection with a transporting means of the type shown in FIG. 13 rather than a transporting means including a reciprocating carriage.

What is claimed is:

1. A test strip of the type which, after being dipped in a liquid such as urine, will assume a color indicative of a property of the liquid, comprising a transparent backing through which light can freely pass, a color-reaction paper for assuming a given degree of a given color when detecting the intensity of a given property of a liquid in which the paper is immersed, said color-reaction paper being situated on one side of but being spaced from said backing, and fastening means situated between the paper and backing and fastening the paper to the backing, said fastening means having at least the same area as said paper and engaging the latter throughout its entire area which is directed toward the backing, and said fastening means being substantially opaque and non-reflecting with respect to light, so that light will pass freely through said backing at portions thereof not engaged by said fastening means while light will be reflected from said color-reaction paper while remaining substantially uninfluenced by said fastening means and backing.

2. The combination of claim 1 and wherein said fastening means has an area substantially equal to that of said paper.

3. The combination of claim 2 and wherein at least one additional color-reaction paper and one additional fastening means are carried by said backing with the additional fastening means situated between said additional paper and backing, said additional color-reaction paper having a standard color for providing a standard with respect to which the color of said first-mentioned color-reaction paper can be measured.

4. The combination of claim 2 and wherein a plurality of said color-reaction papers and a plurality of said fastening means are all carried by said backing, the latter being elongated and said plurality of papers and fastening means being distributed longitudinally along said backing while being spaced one from the next along said backing, the several color-reaction papers respectively indicating different properties with respect to a liquid in which all of the papers are dipped.

5. The combination of claim 2 and wherein said fastening means is a layer of adhesive material adhering on the one hand to said backing and on the other hand to said paper and has a color providing the layer of adhesive material with the substantially opaque, non-reflective properties with respect to light.

6. The combination of claim 5 and wherein the color of said adhesive layer is black.

7. In a method for utilizing a test strip composed of a transparent backing on the side of which there is a color-reaction paper fastened to the backing by a fastening means between the paper and backing which is substantially opaque and non-reflective with respect to liquid with respect to which the color-reaction paper will assume a given color, comprising the steps of directing light along a given optical axis and while maintaining the test strip perpendicular to said axis providing between the light and test strip a movement according to which the light passes first through the backing and then impinges on the color-reaction paper to be reflected thereby, generating a firt signal from the light which passes through said backing, generating from the light which reflects from said color-reaction paper a second signal indicative of the color of the reaction paper, and initiating the generation of said second signal at a given time interval after termination of said first signal by intersection of said color-reaction paper with said optical axis.

8. In a method as recited in claim 7 and including the step of generating a reference signal from a standard color-reaction paper prior to generation of said first and second signals, and then comparing said second signal with said reference signal for determining a property of the liquid.

9. In a method as recited in claim 7 and wherein a plurality of color-reaction papers respectively indicating different properties of a liquid in which they have previously been immersed are respectively fastened to the backing and distributed longitudinally along the latter by a plurality of the fastening means, respectively, which are substantially opaque and non-reflective with respect to light, and moving the test strip across the optical axis so that a plurality of said first signals respectively alternate with a plurality of second signals with each second signal being generated after the immediately preceding first signal after said given time interval.

10. In a method for utilizing a test strip having a transparent backing and a color-reaction paper situated on one side of said backing with a fastening means situated between the paper and backing for fastening the paper to the backing with the fastening means being substantially opaque and non-reflective with respect to light, the steps of directing light along a predetermined optical axis, moving the test strip perpendicularly across the optical axis with the backing first intersecting the optical axis and the color-reaction paper then intersecting the optical axis, so that light passes first freely through the backing and then is reflected by the color-reaction paper, generating a pair of signals first with light which has passed through the transparent backing and then with light which is reflected from the color-reaction paper, and utilizing the great difference between these signals for achieving a clear indication of the signal from light reflection by the color-reaction paper.

11. In an apparatus for utilizing a test strip having a transparent backing, a color-reaction paper on one side of the backing, and a fastening means between the paper and backing fastening the paper to the backing with the fastening means being substantially opaque and non-reflective with respect to light, optical means for directing light along a predetermined optical axis, transporting means connected with the test strip for transporting the latter perpendicularly across the optical axis in a manner permitting the light traveling along the optical axis first to pass freely through the backing and then to be reflected by the color-reaction paper, a pair of detecting means one of which is situated at the side of the test strip opposite from the optical means to receive light traveling through the transparent backing and the other of which is situated on the same side of the test strip as the optical means for receiving light reflected by the color-reaction paper, whereby each detecting means receives light sharply different from the light received by the other detecting means during an interval different from the interval during which the other detecting means receives light, and electrical means operatively connected with the pair of detecting means for responding to the sharp difference between the light received by the pair of detecting means for providing information with respect to the light reflected by the color-reaction paper.

12. The combination of claim 11 and wherein the backing is in the form of an elongated strip while a plurality of the color-reaction papers are distributed longitudinally along the strip, spaced from each other, with a plurality of fastening means respectively situated between the color-reaction papers and the strip fastening the papers to the strip, said transporting means including a pair of rolls on one of which the strip is initially wound and from which the strip is unwound while being wound up on the other of the rolls, with the rolls being situated on opposite sides of the optical axis for transporting the strip across the optical axis.

13. The combination of claim 11 and wherein said transporting means includes a carriage carrying the strip and formed in alignment therewith with an opening through which the light can freely pass after passing through the transparent backing to be received by said one detecting means.

14. The combination of claim 11 and wherein said electrical means includes a control means connected between said pair of detecting means for initiating operation of said other detecting means after said control means detects that the color-reaction paper has reached the optical axis by the reduction in the light received by said one detecting means.

15. The combination of claim 11 and wherein said electrical means includes a timer circuit means for initiating the operation of said transporting means only after the color-reaction paper has had sufficient time to react with respect to a liquid in which the color-reaction paper has previously been immersed.

16. The combination of claim 11 and wherein said electrical means includes a pair of detecting circuit means respectively connected with said pair of detecting means for converting light received thereby into predetermined voltages, and signal-discriminating circuit means connected between said pair of detecting circuit means for discriminating when the light received by said one detecting means has been diminished to an extent indicating that the color-reaction paper has reached the optical axis and for then operating the detecting circuit means connected to said other detecting means.

17. The combination of claim 16 and wherein a computing circuit means is connected with the detecting circuit means which is connected to said other detecting means for computing the signal generated from reflection of light from the color-reaction paper.

18. The combination of claim 17 and wherein said electrical means includes a memory circuit means connected between said computing circuit means and said detecting circuit means which is connected to said other detecting means for memorizing a reference signal to be compared with the signal provided by said detecting circuit means connected to said other detecting means at said computing circuit means, for providing information with respect to the light reflected from the color-reaction paper.

* * * * *